United States Patent [19]
Bachmann et al.

[11] Patent Number: 6,103,733
[45] Date of Patent: Aug. 15, 2000

[54] METHOD FOR INCREASING HDL CHOLESTEROL LEVELS USING HETEROAROMATIC PHENYLMETHANES

[76] Inventors: Kenneth A. Bachmann, 308 E. Sixth St., Perrysburg, Ohio 43551; James T. Slama, 6746 Cloister Ct., Toledo, Ohio 43617

[21] Appl. No.: 09/150,270

[22] Filed: Sep. 9, 1998

[51] Int. Cl.$^7$ ................... A61P 3/00; A61P 9/10; A61K 31/435; A61K 31/4164; A61R 31/40

[52] U.S. Cl. ............ 514/277; 514/399; 514/400; 514/427; 546/343; 546/378; 548/340.1; 548/346.1

[58] Field of Search .............. 548/344.1, 346.1, 548/340.1; 514/399, 700, 277, 427; 546/343, 378

[56] References Cited

U.S. PATENT DOCUMENTS

| | | | |
|---|---|---|---|
| 3,321,366 | 5/1967 | Mussell et al. | 548/344.1 X |
| 3,660,577 | 5/1972 | Buchel, I et al. | 548/344.1 X |
| 3,691,192 | 9/1972 | Buchel, II et al. | 548/344.1 |
| 3,705,172 | 12/1972 | Buchel, III et al. | 548/344.1 |
| 3,711,497 | 1/1973 | Buchel, IV et al. | 548/344.1 |
| 3,711,498 | 1/1973 | Buchel, V et al. | 548/344.1 |
| 3,833,603 | 9/1974 | Buchel, VI et al. | 548/344.1 |
| 3,836,540 | 9/1974 | Van Der Selt et al. | 548/344.1 |
| 4,343,811 | 8/1982 | Hurnaus et al. | 424/274 |
| 4,891,220 | 1/1990 | Donzis | 424/88 |
| 4,916,126 | 4/1990 | Traxler et al. | 514/183 |
| 4,975,456 | 12/1990 | Creger et al. | 514/466 |
| 4,994,465 | 2/1991 | Trivedi | 514/256 |
| 5,001,148 | 3/1991 | Saunders et al. | 514/459 |
| 5,011,859 | 4/1991 | Jarvi et al. | 514/739 |
| 5,091,540 | 2/1992 | Molinari | 548/344.1 |
| 5,132,424 | 7/1992 | Larsen et al. | 544/251 |
| 5,153,226 | 10/1992 | Chucholowski et al. | 514/617 |
| 5,157,025 | 10/1992 | Aberg et al. | 514/80 |
| 5,166,398 | 11/1992 | Creger | 560/32 |
| 5,173,487 | 12/1992 | Saunders et al. | 514/227.5 |
| 5,180,717 | 1/1993 | Gammill et al. | 514/63 |
| 5,200,424 | 4/1993 | Granzer et al. | 514/450 |
| 5,204,373 | 4/1993 | Pearce | 514/720 |
| 5,212,164 | 5/1993 | Biller et al. | 514/108 |
| 5,248,688 | 9/1993 | Dudrick | 514/396 |
| 5,278,171 | 1/1994 | Wannamaker et al. | 514/307 |
| 5,288,757 | 2/1994 | Picard et al. | 514/593 |
| 5,296,508 | 3/1994 | Pearce | 514/510 |
| 5,298,497 | 3/1994 | Tschollar et al. | 514/91 |
| 5,304,548 | 4/1994 | Gammill et al. | 514/63 |
| 5,312,814 | 5/1994 | Biller et al. | 514/39 |
| 5,348,964 | 9/1994 | Barney et al. | 514/315 |
| 5,350,758 | 9/1994 | Wannamaker et al. | 514/315 |
| 5,364,644 | 11/1994 | Walaszek et al. | 514/574 |
| 5,391,765 | 2/1995 | Pearce et al. | 548/542 |
| 5,393,776 | 2/1995 | Pearce | 514/486 |

OTHER PUBLICATIONS

Cozzi et al., "N–Imadazolylchroman–4–ones, N–Imidazolyl–1–tetralones, and Their Alcohols as Hypolipemic Agents Raising High–Density Lipoproteins", J. Med. Chem. 29, pp. 404–410 (1986).

Slama et al., "Influence of Some Novel N–Substituted Azoles and Pyridines on Rat Hepatic CYP3A Activity", Biochemical Pharmacology, vol. 55, pp. 1881–1892 (1998).

Primary Examiner—Floyd D. Higel
Attorney, Agent, or Firm—MacMillan, Sobanski & Todd, LLC

[57] ABSTRACT

An HDL cholesterol level inducing compound and a method of administering the compound having the structural formula I.

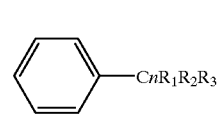

(I)

wherein n is 1 or 2;

$R_1$ is a heteroaromatic substituent independently selected from a five-membered heteroaromatic ring having at least one N heteroatom, a six-membered heteroaromatic ring having at least one N heteroatom, or a fused ring system having at least one five-membered heteroaromatic ring having at least one N heteroatom;

$R_2$ is independently selected from —H or phenyl; and $R_3$ is independently selected from —H, —CH$_3$, —OH, phenyl, phenyl substituted with Cl, OCH$_3$, CH$_3$, or F, fused phenyl ring system, or six-membered heteroaromatic ring having at least one N heteroatom.

7 Claims, 6 Drawing Sheets

METHOD FOR INCREASING HDL CHOLESTEROL LEVELS USING HETEROAROMATIC PHENYLMETHANES

FIELD OF THE INVENTION

This invention relates to heteroaromatic phenylmethanes. More particularly, this invention relates to heteroaromatic phenylmethanes useful as high density lipoprotein cholesterol (HDL) elevating drugs.

BACKGROUND OF THE INVENTION

Recent studies have indicated a pharmacologic elevation of serum high density lipoprotein (HDL) concentrations may be linked to the prevention of atherosclerosis, and subsequently, coronary heart disease. See summary of the second report of the National Cholesterol Education Program (NCEP) Expert Panel on detection, evaluation, and treatment of high blood cholesterol in adults (Adult Treatment Panel II). J.A.M.A. 148:36–69, 1988. Atherosclerosis is one of the leading causes of death in modern societies, and is initiated by lipid, mostly cholesterol, accumulation in the arterial wall. The accumulation triggers a cascade of events, resulting in the formation of an atherosclerotic plaque, and symptomatic atherosclerotic disease. See Wissler, R W: Update on the pathogenesis of atherosclerosis. Am. J. Med. 91: (supp. 1B)3S–9S, 1991, and Ross, R.: The pathogenesis of atherosclerosis: a perspective for the 1990s. Nature 362:801–809, 1993. The lipoproteins that transport cholesterol are classified into three major lipoprotein classes in the serum: High density (HDL), low density (LDL) and very low density (VLDL) lipoproteins. The two main subclasses $HDL_2$ and $HDL_3$ have been identified within the HDL density range. Further, apoproteins A1 and A2 are the major apoprotein constituents of HDL, and have been considered to be anti-atherogenic due to their abilities to transport cholesterol from arteries to the liver for catabolism and excretion. See Furchart J. and Ailhaud G.: Apoliprotein A-containing lipoprotein particles: Physiological role, quantification and clinical significance. Clin Chem. 38:793–797, 1992. HDL cholesterol is often referred to as "good" cholesterol since the negative association between serum HDL concentration and coronary heart disease is at least as strong as the positive association between low density lipoprotein (LDL) and coronary heart disease.

Management of hyperlipidermias constitutes a major health problem in the United States. A number of useful lipid-lowering (antiatherosclerotic) agents are currently marketed. However, these drugs all suffer from some disadvantage such as, but not limited to, patient non-compliance, production of side effects, or sub-optimal effects on serum cholesterol at tolerated doses. It is believed that none of the currently available drugs was developed to increase HDL-cholesterol and accordingly those with the greatest effects on HDL-cholesterol are capable of elevating this lipoprotein by 10–25%. It will be appreciated that an improved antiatherosclerotic drug designed to substantially elevate serum HDL-cholesterol is desireable. See P. Greenspan, "Drugs Affecting Cholesterol Metabolism," Georgia Pharmacist Quarterly, 70, 1–2, 1993.

It is known that epileptic subjects, treated with anticonvulsants such as phenobarbital and/or phenytoin had higher levels of HDL-cholesterol than matched patients without epilepsy. See Luoma P. Myllyla V and Hokkanen E: Relationship between plasma High-Density Lipoprotein Cholesterol and anticonvulsant levels in epileptics. J. Cardiovascular Pharmacol. 4:1024–1027, 1982. It was speculated that hepatic microsomal enzyme induction may play a role in the elevation of serum HDL levels and thus in the reduction of cholesterol accumulation, since several of the most widely used anticonvulsant drugs are inducers of hepatic mixed function oxidases. Phenobarbital was known to be an inducer of the cytochromes P450, and prospective experiments demonstrated that phenobarbital could elicit increases in total serum HDL cholesterol/total cholesterol ratios. See Luoma P. Marniemi J, and Sotaniemi E.: The effects of phenobarbital on serum high densitylipoprotein subfractions and apolipoproteins. Res. Comm. Chem. Path Pharmacol. 62:125–128,, 1988 and Chao, Y. Pickett, C. Yamin T, Guo L. Alberts A, and Kroon P.: Phenobarbital induces rat liver apolipoprotein A1 mRNA. Molec. Pharmacol 27:394–398, 1984. Phenobarbital was also noted to increase HDL-cholesterol and apoA1 in rats, though the mechanism of this elevation is not yet understood. See Chao, Y. Pickett, C. Yamin T, Guo L. Alberts A, and Kroon P.: Phenobarbital induces rat liver apolipoprotein A1 mRNA. Molec. Pharmacol 27:394–398, 1984.

Based upon the foregoing, it has been found that the elevation of serum HDL-cholesterol levels can be accomplished by the selective induction of hepatic cylochrome P450IIIA (CYP3A) activity. In accordance with the present invention, a family of related compounds have been found to cause a significant elevation of serum HDL cholesterol concentration from 20% to greater than 200%. The family of related compounds are substituted phenylmethanes linked to a heteroaromatic ring containing an unshared pair of electrons in the 3 or 4-N of imidazole or the 4-N of pyridine. The elevation of serum HDL cholesterol levels is accomplished by the selective induction of hepatic cytochrome P450IIIA (CYPA3) activity. Compounds which specifically induce CYPA3 produce significant increases in HDL cholesterol.

Clotrimazole is the lead structure for a series of novel N-substituted imidazoles and related heteroaromatic structures intended to raise HDL cholesterol levels. Triphenylmethyl substituted imidazoles were synthesized by treating the corresponding triphenylmethyl chloride with imidazole or related heteroaromatic compounds. The structure of the compound had a measurable effect on the ability of the compound to increase the rate of CYP3 A activity.

A heteroaromatic nucleus containing basic nitrogen must be present. Significant activity is achieved using substituted imidazoles, 2-methylimidazole or pyridine. The highest activity is associated with the presence of the triphenylmethyl group on N-1 of imidazole. High magnitude CYP3A induction is found in four substituted triphenylmethyl imidazoles: meta-chloro, para-chloro, meta-fluoro and para-fluoro.

SUMMARY OF THE INVENTION

Briefly, according to the present invention there is provided an HDL cholesterol level inducing compound having the structural formula I:

(I)

wherein, n is 1 or 2;

$R_1$ is a heteroaromatic substituent independently selected from a five-membered heteroaromatic ring having at least one N heteroatom, a six-membered heteroaromatic ring having at least one N heteroatom, or a fused ring system having at least one five-membered heteroaromatic ring having at least one N heteroatom;

$R_2$ is independently selected from —H or phenyl; and $R_3$ is independently selected from —H, —$CH_3$, —OH, phenyl, phenyl substituted with Cl, $OCH_3$, $CH_3$, or F, fused phenyl ring system, or six-membered heteroaromatic ring having at least one N heteroatom.

In yet another embodiment, there is provided a method for increasing blood serum HDL cholesterol levels in a mammal which comprises administering an effective amount of a compound having the structural formula I.

BRIEF DESCRIPTION OF THE DRAWINGS

Further features and other objects and advantages of this invention will become clear from the following detailed description made with reference to the drawings in which.

DETAILED DESCRIPTION OF THE PREFERRED EMBODIMENTS

We have invented a family of related compounds which cause a significant pharmacological elevation of serum high density lipoprotein (HDL-cholesterol) concentration from 20% to greater than 200%. The effect was demonstrated by direct measurement of HDL-cholesterol levels in serum following administration of the compounds to rats over a period of several days. The effect on HDL cholesterol was paralleled by an elevation in the level of apoprotein A1 (a protein component of HDL) and by elevation of apo A1 messenger RNA in treated animals.

High levels of HDL-cholesterol are considered to be anti-atherogenic due to the ability of HDL to transport cholesterol to the liver for catabolism and excretion. This invention therefore represents a possible medical treatment for atherosclerotic heart disease.

The HDL-cholesterol-inducing drugs which we describe are substituted phenylmethanes linked to a heteroaromatic ring containing an unshared pair of electrons in the 3 or 4-N of imidazole or to the 4-N of pyridine:

For example:

(II)

Where:

Heteromatic=heteroaromatic system with unshared electron pair in 3, or 4-position

X=H or substituent $R_1$=H, phenyl, substituted phenyl or heteroaromatic $R_2$=H, phenyl, or substituted phenyl A correlation between induction of CYP3A and an increase in serum HDL-cholesterol was supported by our early experiments in which selective CYP3A inducers (Clotrimazole, dexamethasone) were administered to rats over a period of several days, and the effect on liver/body weight ratios and on HDL-cholesterol/total cholesterol ratios determined. Pretreatment of animals with dexamethasone or with clotrimazole markedly increased liver/body weight ratios (an indirect sign of increased in cytochrome P450 content). A positive relationship between cytochrome P450 induction and improvement of serum lipid levels was also found. There was also a noteworthy improvement in HDL2/total cholesterol ratios in rats pretreated with dexamethasone and clotrimazole. Since clotrimazole had been shown to be a relatively selective inducer of CYP3 A in rats and in human hepatocytes (see Hostetler K. Wrighton S, Molowa D, Thomas P, Levin W, and Guzelian P.: Coinduction of multiple hepatic cytochrome P450 proteins and their mRNAs in rats treated with imidazole antimycotic agents. Molec. Pharmacol, 35:279–285, 1988): we selected clotrimazole as the lead structure for a series of novel N-substituted imidazoles and related heteroaromatic structures intended to raise HDL-cholesterol levels.

Triphenylmethyl substituted imidazoles were synthesized by treating the corresponding triphenylmethyl chloride with imidazole or related heteroaromatic compound (Scheme 1).

The triphenylmethyl chlorides were in turn available by chlorination of the triphenyl carbinol using $SOCl_2$. Substituted triphenyl carbinols were in turn synthesized through the reaction of benzophenone or a substituted benzophenone with an aryl-Grignard or an aryl-lithium reagent. All compounds submitted for biological testing were characterized by $^1$H-NMR and by microanalysis.

Representative structures of compounds in accordance with the present invention synthesized using standard chemical procedures as well known by one skilled in the art are provided below.

(III)

(IV)

(V)

(VI)

(VII)

(VIII)

(IX)

(X)

(XI)

(XII)

(XIII)

(XIV)

(XV)

(XVI)

(XVII)

(XVIII)

(XIX)

(XX)

(XXI)

(XXII)

(XXIII)

(XXIV)

(XXV)

(XXVI)

(XXVII)

(XXVIII)

(XXIX)

(XXX)

(XXXI)

(XXXII)

(XXXIII)

(XXXIV)

(XXXV)

(XXXVI)

(XXXVII)

(XXXVIII)

(XXXIX)

(XXXX)

(XXXXI)

(XXXXII)

(XXXXIII)

Blood serum HDL cholesterol levels in a mammal may be increased by administering an effective amount of a compound having the structural formula of Compounds I–XXXXIII. The precise dosage to be employed depends upon several factors including the host, the severity of the condition being treated, the mode of administration and the like.

The compounds may be administered in most any suitable manner as well known in the art. Pharmaceutical compositions may be prepared from the compounds, or a pharmaceutically acceptable salt thereof, of a pharmaceutically acceptable level of purity excluding normal pharmaceutical additives such as dilutents and carriers.

Figure 1:
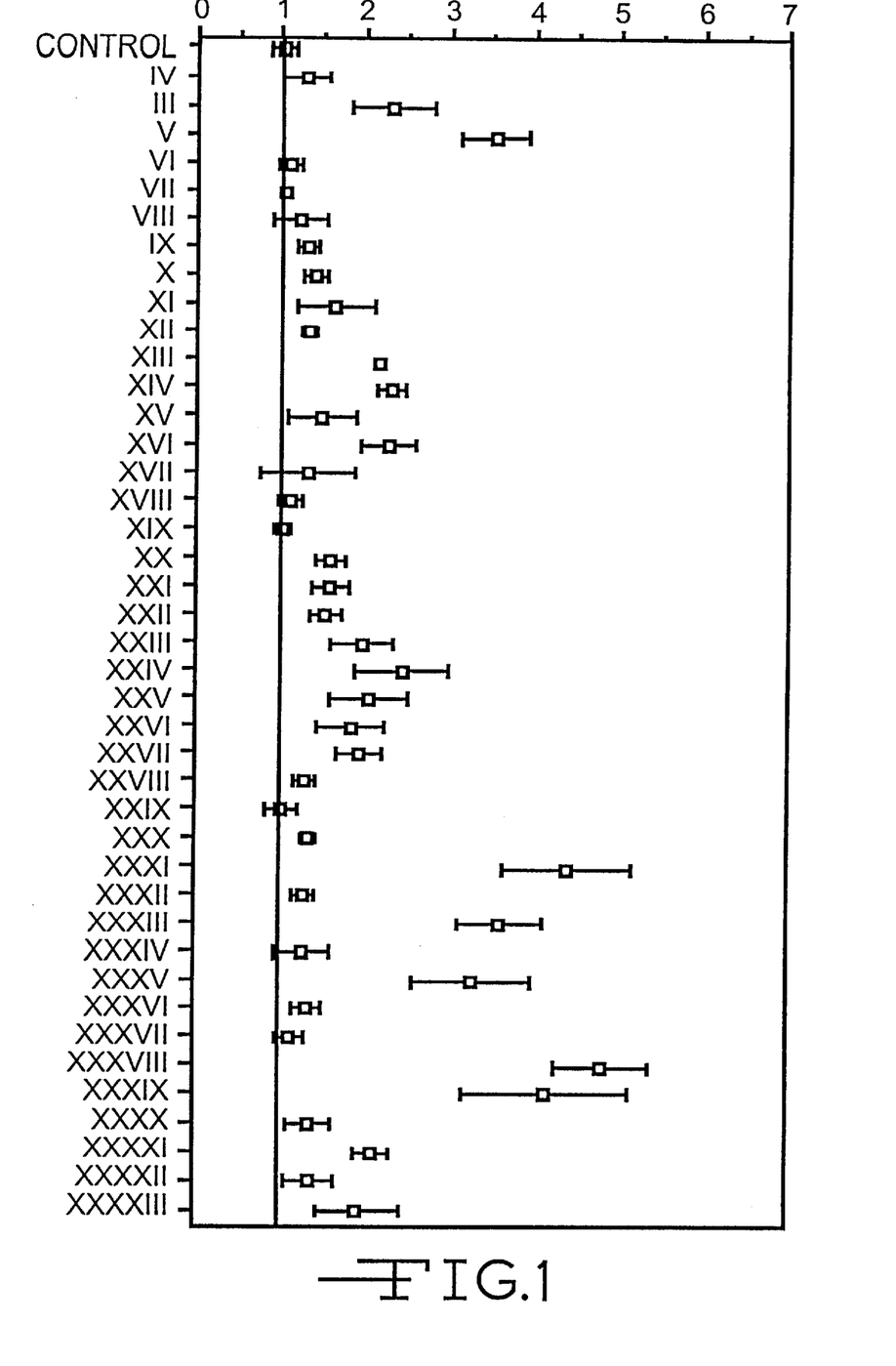
FIG. 1 represents a fold increase in ethosuxinide clearances following an 8-day pretreatment schedule of the azoles.

Using clotrimazole (Compound (III)) as a lead compound, the effect of structure on the ability of a compound to induce CYP3A activity was determined, as measured by the test compound's ability to increase the rate of ethosuximide clearance. Over 40 structural modifications of clotrimazole were tested and significant differences in the ability to induce CYP3A activity was observed. The least active compounds showed no effect, and the most active inducers caused a 4–5 fold increase in ethosuximide clearance rates as shown in FIG. 1.

Compounds (V), (XXXI), (XXXIII), (XXXVIII), and (XXXIX) all induced significantly more CYP3A activity than did the lead compound, clotrimazole (CTZ) Compound (III).

Analysis of the effect of substitution on the ability of a compound to induce CYP3A activity enables us to propose requirements for the induction in vivo. First, a heteroaromatic nucleus containing basic nitrogen must be present. Significant activity (i.e. >2 fold increase in ethosuximide clearance) is achieved only using substituted imidazoles, 2-methylimidazole (XIV), or in one case, pyridine (XVI). Since no heteroaromatic nucleus was found superior to imidazole, and since the synthesis of 1-substituted imidazoles is particularly facile, the series of 1-substituted imidazoles was elaborated. As aromatic substituents are removed from the 1-methyl position of 1-triphenylmethylimidazole (V), yielding 1-diphenylmethylimidazole (XIII) or benzylimidazole (IV), the CYP3A inducing activity is progressively lost. Therefore, it has been found that the highest activity is associated with the presence of the triphenylmethyl group on N-1 of imidazole. A variety of substituents were introduced into a single aryl ring of triphenylmethylimidazole. Most of the monosubstituted 1-triphenylmethylimidazoles produced inducing activity lower than that measured for the unsubstituted member of the series, regardless of the nature of the substituent. High magnitude CYP3A induction (i.e. >3-fold increase in ethosuximide clearance was found in only four substituted triphenylmethyl imidazoles: (XXXI)(metachloro). (XXXIII)(para chloro), (XXXVIII)(metafluoro).

Figure 2:
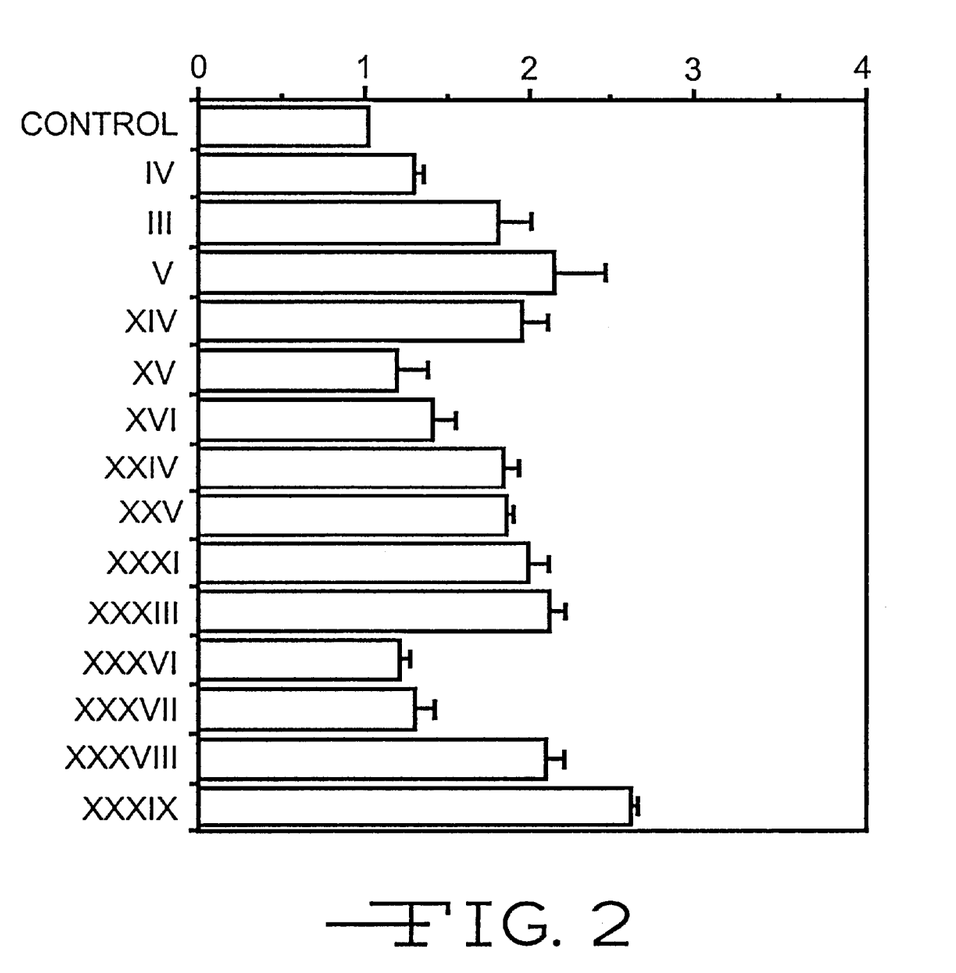
FIG. 2 represents a fold increase of HDL-cholesterol per compound.
Figure 3:
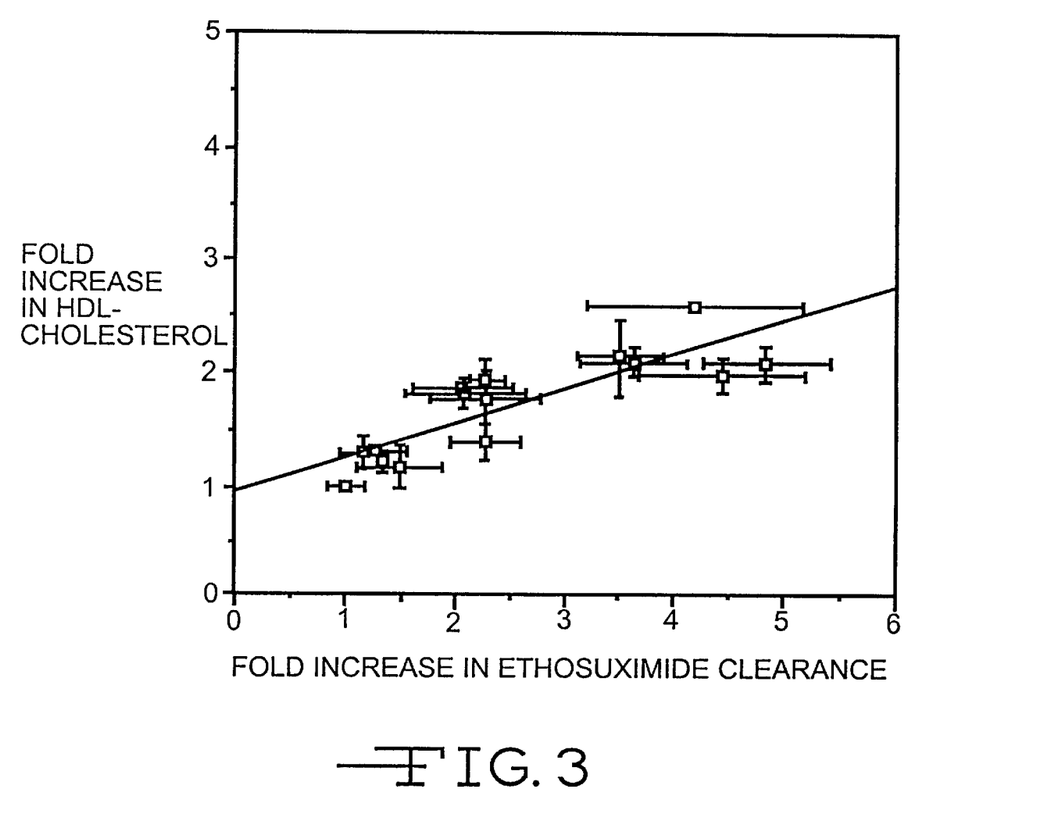
FIG. 3 represents the correlation between mean fold increase in CYP3A activity as measured by ethosuximide clearances and mean fold increase in HDL-cholesterol.

The effect of CYP3A inducers on levels of HDL-cholesterol was determined by administration of the compound by feeding over 8 days followed by sacrifice of the animal and determination of HDL-cholesterol levels. The effects of benzylimidazole (IV), clotrimazole, the five high magnitude CYP3A inducers and four compounds showing intermediate CYP3A inducing activity were evaluated. The effect of the administration of the CYP3A inducers on HDL-cholesterol is shown in FIG. 2. Each of the compounds showed a significant effect on HDL-cholesterol, but the greatest effect was associated with the "high magnitude" CYP3A inducers. The significant linear correlation between the increase in HDL-cholesterol and the increase in ethosuximide clearance is shown in FIG. 3, and supports the belief that the activities are related.

Figure 4:
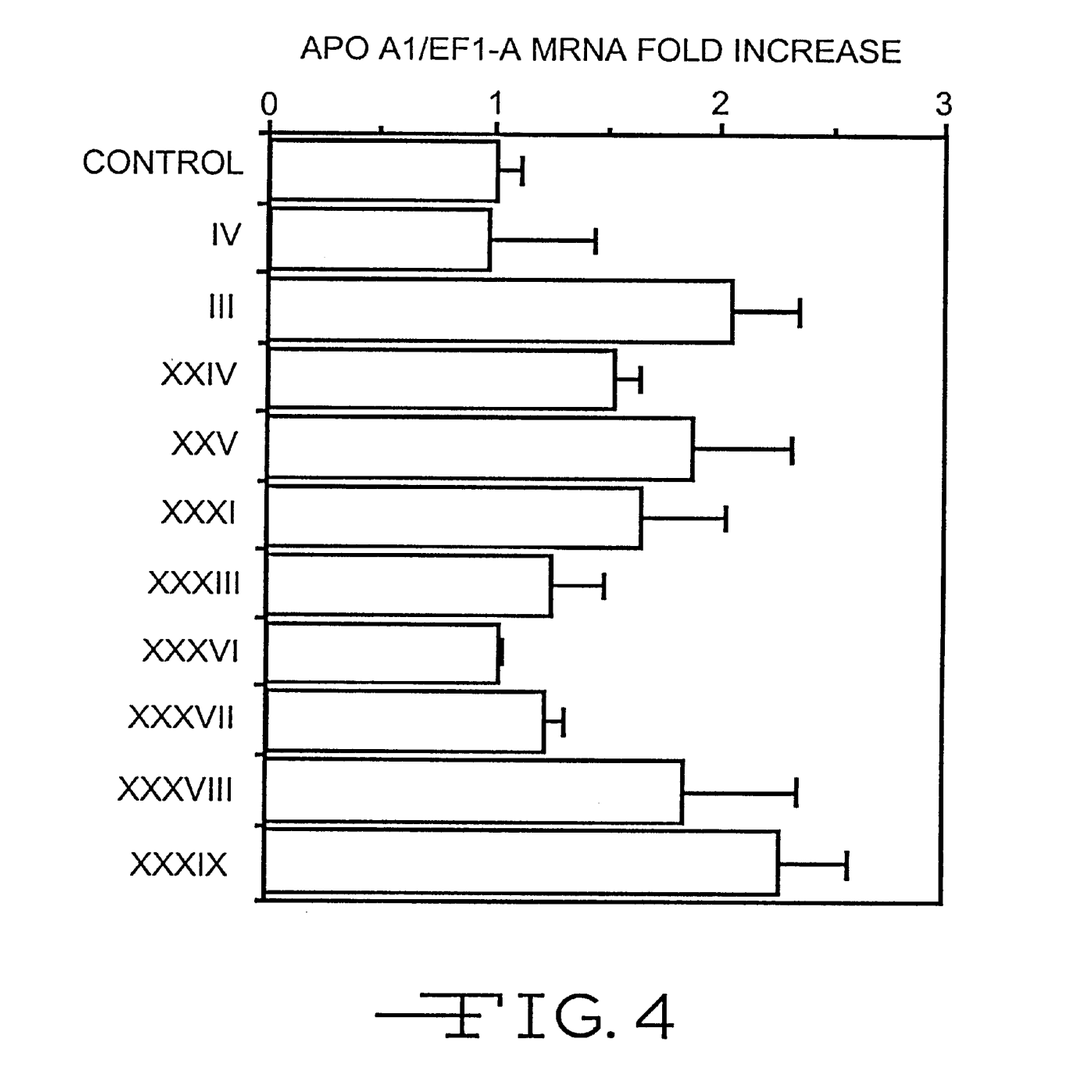
FIG. 4 represents apolipoprotein A-1mRNA/EF-1a mRNA levels relative to control.
Figure 5:
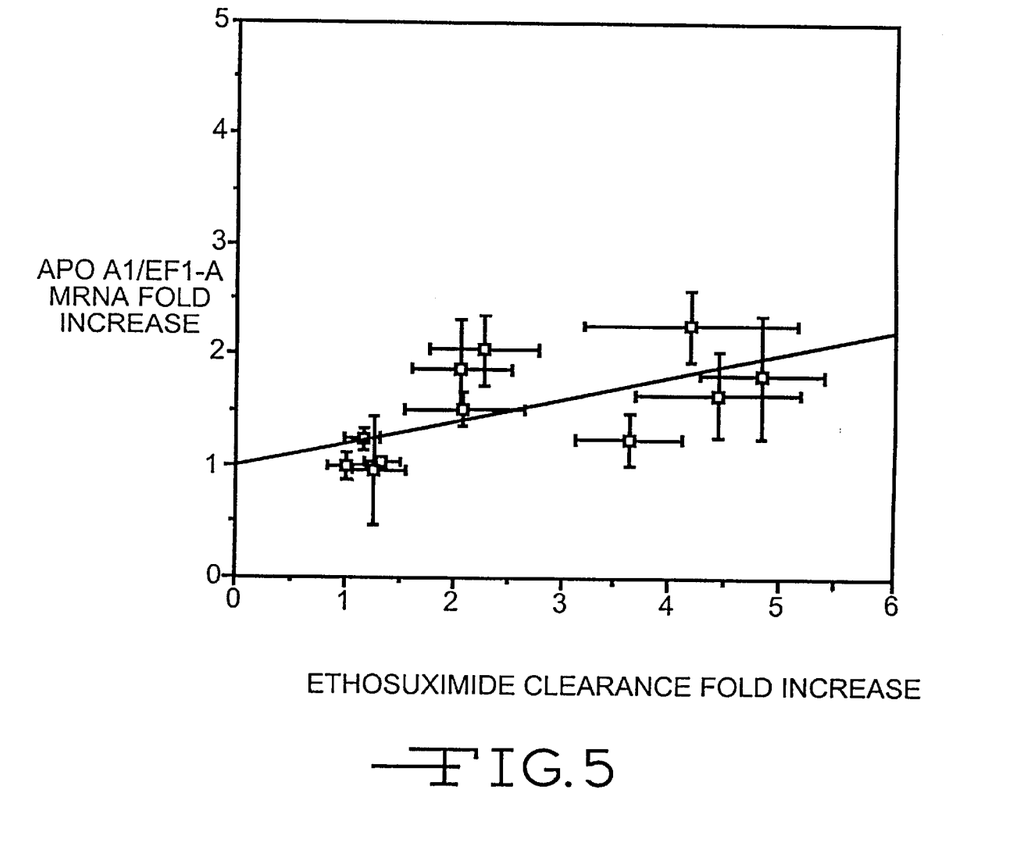
FIG. 5 represents the correlation between ethosuximide clearance fold increase and the apolipoprotein A-1mRNA/EF1-a mRNA fold increase.
Figure 6:
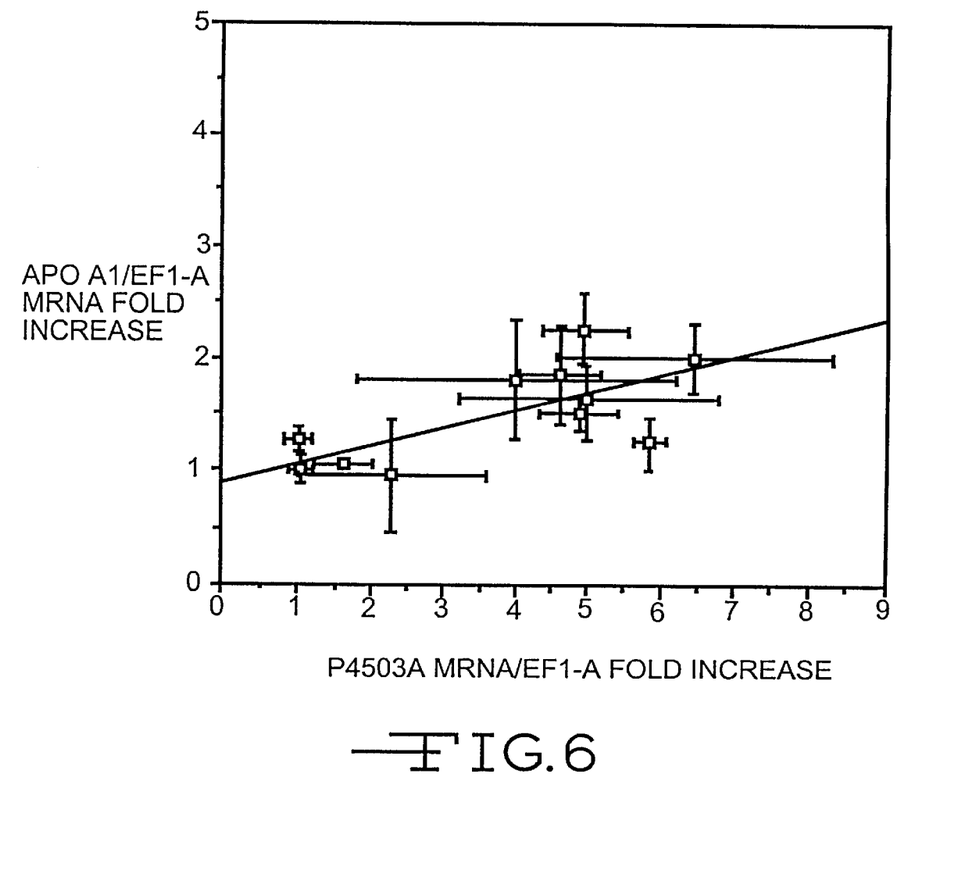
FIG. 6 represents the correlation between apolipoprotein A-1mRNA/EF1amRNA and P4503A mRNA fold increase.

To confirm the belief that these increases in HDL-cholesterol levels were a reflection of increased HDL particle synthesis, we also measured hepatic apoA1 messenger RNA. Increases in apoA1 mRNA implies an increase in the biosynthesis of apoA1, and predicts an increase in circulating levels of HDL-cholesterol. FIG. 4 represents the effects of treatment of rats with CYP3A inducing drugs on the levels of hepatic apoA1 mRNA. Again, a significant increase in the message was associated with CYP3A inducing activity. The direct linear correlation between apoA1 message levels and the increase in rates of ethosuximide clearance is represented in FIG. 5. FIG. 6 demonstrates a correlation between hepatic apoA1 mRNA levels and hepatic CYP3A mRNA levels. This data shown in the figures supports the contention that CYP3A induction causes elevation of apoA1 synthesis.

In view of the foregoing, it has been shown that the administration of the foregoing compounds effectively increased HDL cholesterol levels in rats. Furthermore, it has been shown that there is a connection between increased HDL cholesterol and induced CYP3A activity as follows:

1. All compounds active in inducing CYP3A also increased HDL-cholesterol levels;
2. All compounds inactive in inducing CYP3A failed to increase HDL-cholesterol levels;
3. There was an excellent correlation between increases in CYP3A activity and increases in HDL-cholesterol levels (see FIG. 3);
4. Compounds that increased CYP3A activity and CYP3A mRNA levels in the liver also increased apoA1 mRNA in livers (FIGS. 5 and 6).

The references and documents identified herein are hereby incorporated by reference.

Having described presently preferred embodiments of the present invention, the invention may be otherwise embodied within the scope of the appended claims.

What is claimed is:

1. A method for increasing blood serum HDL cholesterol levels in a mammal which comprises administering an effective amount of a compound having the structural formula I:

wherein, n is 1 or 2;

$R_1$ is a heteroaromatic substituent independently selected from a five-membered heteroaromatic ring having from one to three N heteroatoms, a six-membered heteroaromatic ring having from one to three N heteroatoms, or a fused ring system having at least one five-membered heteroaromatic ring having from one to three N heteroatoms;

$R_2$ is independently selected from —H or phenyl; and

$R_3$ is independently selected from —H, —$CH_3$, —OH, phenyl, phenyl substituted with Cl, $OCH_3$, $CH_3$, or F, fused phenyl ring system, or six-membered heteroaromatic ring having from one to three N heteroatoms.

2. The method of claim 1 wherein said mammal is a human.

3. A method for increasing blood serum HDL cholesterol levels in a mammal which comprises administering an effective amount of a compound having the structural formula selected from the following:

(III)

(IV)

(V)

(VI)

(VII)

(VIII)

(IX)

(X)

(XI)

(XII)

(XIII)

(XIV)

(XV)

(XVI)

(XVII)

(XVIII)

(XIX)

(XX)

(XXI)

(XXII)

(XXIII)

(XXIV)

(XXV)

(XXVI)

(XXVII)

(XXVIII)

(XXIX)

(XXX)

(XXXI)

(XXXII)

(XXXIII)

(XXXIV)

(XXXV)

(XXXVI)

(XXXVII)

(XXXVIII)

(XXXIX)

(XXXX)

(XXXXI)

(XXXXII)

(XXXXIII)

4. The method of claim 1 wherein the six-membered heteroaromatic ring has from one to two N heteroatoms.

5. The method of claim 1 wherein the fused ring system has one five-membered heteroaromatic ring.

6. The method of claim 5 wherein the fused ring system further has a phenyl ring.

7. The method of claim 1 wherein the fused phenyl ring system has two phenyl rings.

* * * * *

UNITED STATES PATENT AND TRADEMARK OFFICE
CERTIFICATE OF CORRECTION

PATENT NO. : 6,103,733
DATED : August 15, 2000
INVENTOR(S) : Bachmann et al.

Page 1 of 1

It is certified that error appears in the above-identified patent and that said Letters Patent is hereby corrected as shown below:

Title page,
List of inventors, "308 E. Sixth St." should be changed to "285 Cedar Ridge Ct."
Also, the following additional inventor should be listed: Taikyun Rho,
5919 Highland Rd., Highland Heights, Ohio 44143.
Item [56] first line of Other Publications, "N-Imadazolylchroman..." should be changed to "N-Imidazolylchroman..."

Column 3,
Line 13, "ethosuxinide" should be changed to "ethosuximide".

Column 8,
Line 60, "CH3" on structure XXIII should be changed to "$CH_3$".

Column 18,
Line 51, "CH3" on the structure XXIII should be changed to "$CH_3$".

Column 22,
Line 35, a carbon-to-carbon double bond should be added on the imidazole ring as follows:

Signed and Sealed this

Twenty-seventh day of November, 2001

Attest:

NICHOLAS P. GODICI
Attesting Officer
Acting Director of the United States Patent and Trademark Office